United States Patent [19]

Stiefel

[11] 4,224,443
[45] Sep. 23, 1980

[54] CHEMICAL PROCESS FOR PREPARATION OF 7-CHLORO-2-METHYL-3,3A-DIHYDRO-2H,9H-ISOXAZOLO(3,2-b)(1,3)-BENZOXAZIN-9-ONE

[75] Inventor: Frank J. Stiefel, Princeton Junction, N.J.

[73] Assignee: Carter-Wallace, Inc., New York, N.Y.

[21] Appl. No.: 142

[22] Filed: Dec. 29, 1978

[51] Int. Cl.$^2$ .......................................... C07D 498/04
[52] U.S. Cl. ................................ 544/95; 424/248.51; 544/90
[58] Field of Search ............................. 544/89, 93, 95

[56] References Cited

U.S. PATENT DOCUMENTS

| | | | |
|---|---|---|---|
| 3,598,814 | 8/1971 | Reisner et al. | 544/95 |
| 3,684,805 | 8/1972 | Reisner et al. | 544/93 X |
| 3,903,083 | 9/1975 | Shen et al. | 544/95 |

*Primary Examiner*—John D. Randolph
*Attorney, Agent, or Firm*—Kevin B. Clarke

[57] ABSTRACT

The compound 7-chloro-2-methyl-3,3a-dihydro-2H,9H-isoxazolo(3,2-b)(1,3)-benzoxazin-9-one is produced by reacting a mixture of tetrahydrofuran and crotonaldehyde with 5-chlorosalicylhydroxamic acid. The compound has demonstrated utility as a uricosuric agent.

3 Claims, No Drawings

IMPROVED CHEMICAL PROCESS FOR PREPARATION OF 7-CHLORO-2-METHYL-3,3A-DIHYDRO-2H,9H-ISOXAZOLO(3,2-b)(1,3)-BENZOXAZIN-9-ONE 7-chloro-2-methyl-3,3a-dihydro-2H,9H-isoxazolo (3,2-b) (1,3) benzoxazin-9-one is a useful compound having valuable pharmacological properties, for example, it is a valuable anti-inflammatory agent, as evidenced by its ability to inhibit the local edema formation characteristic of inflammatory states when administered systemically to warm-blooded animals.

This invention relates to a novel method for the preparation of 7-chloro-2-methyl-3,3a-dihydro-2H,9H-isoxazolo (3,2-b) (1,3) benzoxazin-9-one.

Prior to the present invention, 6-chloro-2-methyl-3,3a-dihydro-2H,9H-isoxazolo (3,2-b) (1,3) benzoxazin-9-one has been prepared by the reaction of 5-chlorosalicylhydroxamic acid (made from 5-chlorosalicylate and hydroxylamine) and crotonaldehyde in the presence of hydrogen chloride and glacial acetic acid to obtain 6-chloro-2-(2-chloropropyl)-2,3-dihydro-3-hydroxy-4H-1,3-benzoxazin-4-one. The latter compound was then cyclized to 7-chloro-2-methyl-3,3a-dihydro-2H,9H-isoxazolo (3,2-b) (1,3) benzoxazin-9-one. Said cyclization can be carried out using organic or inorganic bases in the appropriate solvent. U.S. Pat. No. 3,598,814 discloses and claims 7-chloro-2-methyl-3,3a-dihydro-2H,9H-isoxazolo (3,2-b) (1,3) benzoxazin-9-one and several methods for its manufacture.

All of the prior art processes are characterized by relatively low yield of the desired compound and difficulty in handling. Such low yields are reflected in the cost of producing the compound. It has now been found that if the reaction of 5-chlorosalicylhydroxamic acid with crotonaldehyde is carried out in tetrahydrofuran, improved yields of 7-chloro-2-methyl-3,3a-dihydro-2H,9H-isoxazolo (3,2-b) (1,3) benzoxazin-9-one are obtained. Moreover, the process is more easily handled. The obtaining of better yields and the easier process manipulation all combine to reduce the cost of the drug to a significant degree. It is most surprising that this change of solvents effects the commercial feasibility of the process.

In the practice of the invention 5-chlorosalicylic acid is refluxed with methanol to produce the methyl ester. The methyl ester is combined with hydroxylamine sulfate and treated with an alkali and water then neutralized with acid and the solid 5-chlorosalicylhydroxamic acid is recovered.

A solution of crotonaldehyde in tetrahydrofuran is treated with a hydrogen halide at temperatures of from about 15° to about 35° C. Upon completion of the halide treatment, the solid 5-chlorosalicylhydroxamic acid is added to the solution and the mixture is treated with an aqueous alkali metal hydroxide. The reaction temperature is maintained at from about 25° to about 55° C. during alkali addition depending upon the particular alkali employed. When the alkali addition is completed, the mixture is heated to a temperature of from about 50° to about 90° C., again depending upon the particular alkali employed, and vacuum applied to remove as much of the solvent as possible. A solid precipitate is collected, diluted with water, filtered and then recrystallized from hot isopropanol.

The following non-limiting examples set forth the preferred methods for carrying out the preparation of 7-chloro-2-methyl-3,3a-dihydro-2H,9H-isoxazolo (3,2-b) (1,3) benzoxazin-9-one in accordance with the present invention.

EXAMPLE 1

5-CHLOROSALICYLHYDROXAMIC ACID 50 ml. of concentrated sulfuric acid is added dropwise to a stirred slurry of 200 gm. of 5-chlorosalicylic acid in 400 ml. of methanol. The reaction temperature rises to approximately 35° C. The mixture is heated at reflux with the exclusion of moisture for about 20 hours. The methyl ester separates as an oil and is combined in one portion with 144 gm. of hydroxylamine sulfate in 600 ml. of water at room temperature and rinsed in with methanol. The mixture is stirred and 468 gm. of 50% w/w sodium hydroxide is dripped in while the reaction temperature is maintained at a temperature range of from about 25° to 35° C. After addition of the alkali is completed, 750 ml. of water is added to dissolve the solids while heating to a temperature of about 50° C. The clear solution obtained is allowed to cool to room temperature and neutralized with 140 gm. of concentrated sulfuric acid while the temperature is maintained below about 40° C. The precipitate obtained is diluted with 200 ml. of water, filtered, washed with water and dried at a temperature of about 100° C.

The 5-chlorosalicylhydroxamic acid obtained has a m.p. 218°–220° C., and weighs 182 gm. representing a yield of 84.6%.

EXAMPLE 2

7-CHLORO-2-METHYL-3,3a-DIHYDRO-2H,9H-ISOXAZOLO (3,2-b) (1,3) BENZOXAZIN-9-ONE 400 ml. of tetrahydrofuran is combined with 100 gm. crotonaldehyde and placed in an ice bath. 125 gm. of hydrogen chloride are passed in at a temperature of about 20°–30° C. 182 gm. of 5-chlorosalicylhydroxamic acid is added in one portion and the reaction temperature is allowed to rise to about 31° C. The mixture is stirred at room temperature for about two hours and then 273 gm. of 50% w/w sodium hydroxide diluted with water to 600 ml. is dripped in. The reaction temperature is maintained from about 30° C. to about 40° C. during the alkali addition. When the addition is completed the mixture is heated to about 50° C. in vacuo for approximately one-half hour in order to remove as much tetrahydrofuran as possible. A solid precipitates which is diluted with 600 ml. of water, cooled, filtered and washed with excess water and pulled dry. The crude cake is returned to the reactor and dissolved in 900 ml. of boiling isopropanol, the solution is filtered hot and the reactor rinsed with 100 ml. hot isopropanol. The filtrate is cooled overnight to crystallize. The crystals are filtered, washed with isopropanol and dried at about 100° C. 134 gm. of 7-chloro-2-methyl-3,3a-dihydro-2H,9H-isoxazolo (3,2-b) (1,3) benzoxazin-9-one (m.p. 147° C.–151° C.) for a yield of 57.6% is obtained.

EXAMPLE 3

7-CHLORO-2-METHYL-3,3a-DIHYDRO-2H,9H-ISOXAZOLO (3,2-b) (1,3) BENZOXAZIN-9-ONE 360 ml. of tetrahydrofuran is combined with 90 gm. of crotonaldehyde and placed in an ice bath. 100 gm. of hydrogen chloride are passed into the mixture at 20°–30° C. 158 gm. of 5-chlorosalicylhydroxamic acid is added in one portion and the mixture stirred at 25°–30°

C. for about two hours until the solid dissolves. The mixture is cooled in a water bath and 400 ml. of concentrated ammonium hydroxide diluted with 400 ml. of water is added with stirring. The temperature of the mixture is allowed to rise to about 50° C. during the alkali addition and the mixture is then heated on a steam bath to about 90° C. and a vacuum applied to remove as much tetrahydrofuarn as possible. A solid precipitates while heating. 400 ml. of water are added and the entire mixture is cooled to about 10° C. in an ice bath. The solid is filtered and washed with water and pulled dry. The cake is recrystallized from 800 ml. boiling isopropanol refrigerated overnight. The crystals are filtered, washed with cold isopropanol and dried at about 100° C. 136 gm. 7-chloro-2-methyl-3,3a-dihydro-2H, 9H-isoxazolo (3,2-b) (1,3) benzoxazin-9-one (m.p. 144°–148° C.) for a yield of 67% is obtained.

Clinical evaluation of 7-chloro-2-methyl-3,3a-dihydro-2H,9H-isoxazolo (3,2-b) (1,3) benzoxazin-9-one, demonstrated hypouricemic activity at daily doses of 1.0 to 2.0 gm. in twenty patients. The average pretreatment serum uric acid level was 4.9±0.32 mg./100 ml. compared to 2.25±0.21 mg./100 ml. post-treatment.

The following table sets forth the results obtained in a controlled dose-response serum uric acid study wherein 7-chloro-2-methyl-3,3a-dihydro-2H,9H-isoxazolo(3,2-b) (1,3)-benzoxazin-9-one was administered to twenty patients at two different daily dose levels (1.0 g. and 2.0 gm.) for twelve weeks. The serum uric acid in a similar group of ten patients given aspirin 2.4 gm./day for twelve weeks in also shown for comparative purposes.

TABLE 1

| Dose, gm./day | Total No. Patients | Serum Uric Acid Levels (mg./100 ml.) | |
|---|---|---|---|
| | | Pretreatment | Post-treatment |
| Compound of Example 2 Single dose of 1.0 gms. | 10 | 4.7 ± .31 | 2.4 ± .17 |
| Compound of Example 2 Single dose of 2.0 gms. | 10 | 5.2 ± .34 | 2.1 ± .25 |
| Aspirin 4 doses of .6 gm. each | 10 | 5.3 ± .35 | 4.0 ± .32 |

The results set forth in the table clearly demonstrate dose related uricosuric activity of the compound whereas aspirin at the doses administered did not significantly effect the serum uric acid levels.

Moreover, in another study subjects where given either aspirin 2.4 gm./day or the compound of Example 2, 2.0 gm./day for seven days. In the subjects receiving the compound of Example 2 there was no increase in fecal blood loss over pretreatment levels. Individuals receiving aspirin demonstrated fecal blood loss which was 3-4 times greater than pretreatment values.

The pharmaceutical compositions of the present invention are prepared by incorporating the active ingredient with a suitable pharmaceutical carrier. The carrier must be of such a nature that the composition may be administered systemically to warmblooded animals. The term "systemically" as used herein, means a mode of administration whereby the active ingredient, when given to warmblooded animals, is effective in the whole body and not merely at the locus of application. This includes parenteral and other methods of administration.

The active ingredient is preferably administered orally in the form of tablets or capsules. Suitable pharmaceutical carriers which can be used include, for example, starch, lactose, sucrose, glucose, gelatin and the like. When the composition is in the form of a solid, the active ingredient is generally in an amount of from about 25 to about 95% by weight of the total composition.

The active ingredient can also be dissolved in liquid pharmaceutical carriers such as, for example, propylene glycol, polyethylene glycol, water, saline, and mixtures thereof, to form a solution suitable for injection. Such injectable solutions generally contain from about 0.05 grams to about 30 grams active per 100 ml. of solution.

What is claimed is:

1. In the process for preparing 7-chloro-2-methyl-3,3a-dihydro-2H,9H-isoxazolo (3,2-b) (1,3) benzoxazin-9-one wherein a solution of crotonaldehyde is reacted with 5-chlorosalicylhydroxamic acid, the improvement which comprises preparing said solution by combining tetrahydrofuran and crotonaldehyde at reduced temperatures and thereafter introducing a hydrogen halide into said solution at temperatures of from about 15° to about 35° C.

2. The process of claim 1 wherein said hydrogen halide is hydrogen chloride.

3. The process of claim 1 wherein said hydrogen halide treatment takes place at temperatures ranging from 20° to 30° C.

* * * * *